United States Patent [19]

Huang et al.

[11] Patent Number: 5,498,817
[45] Date of Patent: Mar. 12, 1996

[54] ISOPARAFFIN/OLEFIN ALKYLATION OVER VACANCY-CONTAINING TITANOMETALLATE MOLECULAR SIEVES

[75] Inventors: Tracy J. Huang, Lawrenceville, N.J.; Charles T. Kresge, West Chester, Pa.

[73] Assignee: Mobil Oil Corporation, Fairfax, Va.

[21] Appl. No.: 308,898

[22] Filed: Sep. 20, 1994

[51] Int. Cl.$^6$ ........................................ C07C 2/58
[52] U.S. Cl. .................... 585/709; 585/721; 585/722; 585/732
[58] Field of Search .................... 585/709, 721, 585/722, 732

[56] References Cited

U.S. PATENT DOCUMENTS

| | | | |
|---|---|---|---|
| 3,236,671 | 2/1966 | Dybalski et al. | 106/277 |
| 3,644,565 | 2/1972 | Biale | 585/722 |
| 3,647,916 | 3/1972 | Caesar et al. | 585/722 |
| 3,655,813 | 4/1972 | Kirsch et al. | 585/722 |
| 3,738,977 | 6/1973 | Biale | 526/108 |
| 3,917,738 | 11/1975 | Fenske et al. | 585/722 |
| 4,176,090 | 11/1979 | Vaughan et al. | 252/455 Z |
| 4,384,161 | 5/1983 | Huang | 585/722 |
| 4,831,005 | 5/1989 | Aufdembrink | 502/242 |
| 4,831,006 | 5/1989 | Aufdembrink | 502/242 |
| 5,155,076 | 10/1992 | Moini | 502/63 |
| 5,256,617 | 10/1993 | Moini | 502/351 |
| 5,304,698 | 4/1994 | Husain | 585/722 |
| 5,371,309 | 12/1994 | Moini | 585/407 |

*Primary Examiner*—Ponnathapura Achutamurthy
*Attorney, Agent, or Firm*—Alexander J. McKillop; Dennis P. Santini; Robert B. Furr, Jr.

[57] ABSTRACT

The invention provides a process for alkylating an olefin with an isoparaffin comprising contacting an olefin-containing feed in the presence of a thermally stable composition comprising a non-swellable layered chalcogenide of an element having an atomic number of 4, 5, 12 to 15, 20 to 33, 38 to 51, 56 to 83 and greater than 90, inclusive, said layered metal chalcogenide comprising an interspathic polymeric chalcogenide of an element selected from Groups IB, IIB, IIIA, IIIB, IVA, IVB, VA, VB, VIA, VIIA, and VIIIA of the Periodic Table.

2 Claims, No Drawings

ISOPARAFFIN/OLEFIN ALKYLATION OVER VACANCY-CONTAINING TITANOMETALLATE MOLECULAR SIEVES

FIELD OF THE INVENTION

The present invention relates to the art of improving octane rating of gasoline by alkylating an isoparaffin with an olefin. More particularly, the invention relates to a method for alkylating an isoparaffin with an olefin in the presence of a vacancy-containing titanometallate molecular sieve.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ olefins", 27 *Ind Eng. Chem Res.*, 381–397, (1988). For a survey of hydrofluoric acid catalyzed alkylation, see 1 *Handbook of Petroleum Refining Processes* 23–28 (R. A. Meyers, ed. 1986).

With the increasing demands for octane and the increasing environmental concerns, it has been desirable to develop an alkylation process employing safer, more environmentally acceptable catalyst systems. Specifically, it is desirable to provide an industrially viable alternative to the currently used hydrofluoric and sulfuric acid alkylation processes. Consequently, substantial efforts have been made to develop a viable isoparaffin-olefin alkylation process which avoids the environmental and safety problems associated with sulfuric and hydrofluoric acid alkylation while retaining the alkylate quality and reliability characteristic of these well-known processes. Research efforts have been directed toward solid as well as liquid alkylation catalyst systems, as reflected in the following references.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$–$C_3$ olefins using certain crystalline aluminosilicate zeolite catalysts in a fixed-, moving- or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5$+ paraffins such as Udex raffinate or $C_5$+ olefins to the alkylation reactor feed and the use of specific reactant proportions, halide adjuvants, etc.

U.S. Pat. No. 3,236,671 discloses an alkylation reaction wherein crystalline aluminosilicate zeolites having silica to alumina mole ratios above 3 are used. The reference also discloses the use of various metals exchanged and/or impregnated on such zeolites.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio. According to the patent, problems arise in the use of solid catalyst in that they appear to age rapidly and cannot perform effectively at high olefin space velocity and the patent teaches the above solution to rectify the problem utilizing a zeolite alkylation catalyst.

The article entitled "Fixed Bed Catalytic Process to Produce Synthetic Lubricants from Decene-1", IND. ENG. CHEM. PROD. RES. DEV., Vol. 22, No. 4 (1983) teaches oligomerizing olefin to produce fluids with lubricating properties using a silica-$BF_3$-water catalyst. The authors further teach that with this system much of the $BF_3$ can be recycled to minimize $BF_3$ consumption and disposal problems. The reference teaches that water is a necessary component of the system and that in its absence a $BF_3$-silica catalyst rapidly deactivates.

In U.S. Pat. No. 4,308,414, an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 5,304,698 to Husain teaches a process for alkylating an olefin with an isoparaffin comprising contacting an olefin-containing feed with an isoparaffin-containing feed with a crystalline microporous material under alkylation conversion conditions including temperature at least equal to the critical temperature of the principal component of the feed and pressure at least equal to the critical pressure of the principal component of the feed.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

Various approaches have been taken to provide layered materials of enhanced interlayer distance having thermal stability. Most techniques rely upon the introduction of an inorganic "pillaring" agent between the layers of a layered material. For example, U.S. Pat. No. 4,216,188 incorporated herein by reference discloses a clay which is cross-linked with metal hydroxide prepared from a highly dilute colloidal solution containing fully separated unit layers and a cross-linked agent comprising a colloidal metal hydroxide solution. However, this method requires a highly dilute forming solution of clay (less than 1 g/l) in order to effect full layer separation prior to incorporation of the pillaring species, as well as positively charged species of cross linking agents. U.S. Pat. No. 4,248,739, incorporated herein by reference, relates to stable pillared interlayered clay prepared from smectite clays reacted with cationic metal complexes of metals such as aluminum and zirconium. The resulting products exhibit high interlayer separation and thermal stability.

U.S. Pat. No. 4,176,090, incorporated herein by reference, discloses a clay composition interlayered with polymeric cationic hydroxy metal complexes of metals such as aluminum, zirconium and titanium. Interlayer distances of up to 16A are claimed although only distances restricted to about 9A are exemplified for calcined samples. These distances are essentially unvariable and related to the specific size of the hydroxy metal complex.

Silicon-containing materials are believed to be a highly desirable species of intercalating agents owing to their high thermal stability characteristics. U.S. Pat. No. 4,367,163, incorporated herein by reference, describes a clay intercalated with silica by impregnating a clay substrate with a silicon-containing reactant such as an ionic silicon complex, e.g., silicon acetylacetonate, or a neutral species such as $SiCl_4$. The clay may be swelled prior to or during silicon impregnation with a suitable polar solvent such as methylene chloride, acetone, benzaldehyde, tri- or tetraalkylammonium ions, or dimethylsulfoxide. This method, however, appears to provide only a monolayer of intercalated silica resulting in a product of small spacing between layers, about 2–3 A as determined by X-ray diffraction.

Thus while it would be desirable to substitute a solid alkylation catalyst for the liquid catalysts described above, solid catalysts have not proven in the past to be commercially viable alternatives to liquid acid catalysts due to problems with catalyst longevity and alkylate product quality.

SUMMARY OF THE INVENTION

The present invention includes a process for alkylating an olefin with an isoparaffin comprising contacting an olefin-containing feed with an isoparaffin-containing feed with a thermally stable composition comprising a non-swellable layered chalcogenide of an element having an atomic number of 4, 5, 12 to 15, 20 to 33, 38 to 51, 56 to 83 and greater than 90, inclusive, said layered metal chalcogenide comprising an interspathic polymeric chalcogenide of an element selected from Groups IB, IIB, IIIA, IIIB, IVA, IVB, VA, VB, VIA, VIIA, and VIIIA of the Periodic Table.

The process of the invention converts a feedstock containing at least one isoparaffin having from 4 to 8 carbon atoms and at least one olefin having from 2 to 12 carbon atoms to a product stream containing a higher molecular weight isoparaffin. The process further includes a process for alkylating an olefin with an isoparaffin comprising contacting an olefin-containing feed with an isoparaffin-containing feed with the layered material of the invention under alkylation conversion conditions.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

Isoparaffin:olefin ratios in the reactor feed typically range from about 1:1 to about 100:1 to produce a high-octane isobutane:butene alkylate product at industrially useful yields. Higher isoparaffin:olefin ratios may also be used, however limited availability of produced isoparaffin within the refinery coupled with the relatively high cost of purchased isoparaffin favor isoparaffin:olefin ratios within the ranges listed above.

An internal I/O of above 500 in the reactor can be desirable and an internal I/O ratio of above about 1000 is preferred. The high internal I/O ratio can be achieved by recycling part of the reactor effluent or by back-mixing the reactor contents.

Process Conditions

The present alkylation process can be conducted in liquid phase, critical fluid phase, or vapor phase, using fixed-bed, moving-bed, or slurry reactor configurations.

The present alkylation process is suitably conducted at temperatures from about 0° C. up to about 500° C., preferably from about 25° C. to about 250° C.

Operating pressure is similarly controlled to maintain the principal component of the feed in the liquid or the supercritical state, and is suitably from about 0 to about 2000 psig, preferably from about 150 to about 1000 psig.

Hydrocarbon flow through the alkylation zone containing the catalyst is typically controlled to provide olefin weight hourly space velocity (WHSV) sufficient to convert about 99 percent by weight of fresh olefin to alkylate product. Typical WHSV values fall within the range of from about 0 01 to about 10 hr$^{-1}$, preferably within the range of from about 0.01 to about 5 hr$^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

The deactivated catalyst can be oxidatively or hydrogenatively regenerated. The hydrogenative regeneration is suitably conducted under pressure in the presence of hydrogen at a temperature higher than the alkylation temperature. The presence of a hydrogenation component such as Pt or Pd can facilitate the hydrogenative regeneration.

Catalysts

U.S. Pat. Nos. 4,831,005; 4,831,006 and 4,929,587, the entire disclosures of which are expressly incorporated herein by reference, describe various methods for intercalating layered materials termed titanometallate-type layered metal oxides, wherein each layer of the metal oxide has the general formula $$[M_x\square_y Z_{2-(x+y)}O_4]q-$$

wherein M is at least one metal of valence n wherein n is an interger between 0 and 7, $\square$ represents a vacancy site, Z is titanium, and wherein $$q=4y-x(n-4),$$

and $$0<x+y<2.$$

These intercalating methods involve the placement of polymeric oxides, such as silica, between the layers of the layered material.

Further description of various titanometallate-type layered materials and their methods of preparation can be found in the following references:

Reid, A. F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough; J. B., Wiseman, P. J. *J. Solid State Chem.* 1983, 49 300. The infinite trans-edge shared layer structure of the vacancy titanates instead of the sheared 3-block structure of, for example, $Na_2Ti_3O_7$, or the sheared 4-block structure of, for example, $K_2Ti_4O_9$, may reduce or eliminate shearing of the layers as a possible mechanism for thermal or hydrothermal decomposition of the calcined intercalated material.

The layered metal oxide starting material may be initially treated with a "propping" agent comprising a source of organic cation, such as organoammonium cation, in order to effect an exchange of the interspathic cations resulting in the layers of the starting material being propped apart. Suitable organoammonium cations include such as n-dodecylammonium, n-octylammonium, n-heptylammonium, n-hexylammonium, n-butylammonium and n-propylammonium. During this propping or swelling step it is important to maintain a low hydrogen ion concentration to prevent decomposition of the vacancy titanate structure as well as to prevent preferential sorption of hydrogen ion over the propping agent. A pH range of 6 to 10, preferably 7 to 8.5 is generally employed during treatment with the propping agent.

The foregoing treatment results in the formation of a layered metal oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion.

After the ion exchange, the organic-"propped" species may be treated with a solution of a cationic hydroxyaluminum complex. Such complexes and solutions thereof are described in U.S. Pat. No. 4,176,090, the entire disclosure of which is expressly incorporated herein by reference. These complexes may have the formula $Al_{2+n}(OH)_{3n}X_6$, wherein n has a value from 4 to 12 and X is selected from the group consisting of $Cl^-$, $Br^-$, $NO_3^-$ and $CO_3^-$. Upon hydrolysis up to about 10% of the aluminum of these complexes may be tetrahedrally coordinated, the remainder of the aluminum being octahedrally coordinated. An example of the hydrolyzed complex is a Keggin ion of the formula $[Al_{13}O_4(OH)_{24}(H_2O)_{12}]^{7+}$ It is preferred that the organic cation deposited between the layers be capable of being removed from the pillared material without substantial disturbance or removal of the interspathic aluminum. For example, organic cations such as n-octylammonium may be removed by exposure to elevated temperatures, e.g., calcination, in nitrogen or air, or by chemical oxidation.

These layered products, especially when calcined, exhibit high surface area and thermal and hydrothermal stability making them highly useful as catalysts or catalytic supports, for hydrocarbon conversion processes.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

The layered material catalyst described herein can optionally be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition, impregnated therein or intimately physically admixed therewith. Such component can be impregnated in, or on, the layered material such as, for example, by, in the case of platinum, treating the layered material with a solution containing a platinum metal-containing ion. Thus, suitable platinum compounds for this purpose include chloroplatinic acid, platinous chloride and various compounds containing the platinum amine complex.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed by the thermal treatment, atmospheric pressure is preferred simply for reasons of convenience.

Prior to its use in organic conversion processes described herein, the layered material catalyst should usually be dehydrated, at least partially. This dehydration can be done by heating the crystals to a temperature in the range of from about 200° C. to about 595° C. in an atmosphere such as air, nitrogen, etc., and at atmospheric, subatmospheric or superatmospheric pressures for between about 30 minutes and to about 48 hours. Dehydration can also be performed at room temperature merely by placing the layered material in a vacuum, but a longer time is required to obtain a sufficient amount of dehydration.

The layered material catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the layered material can be extruded before drying or partially dried and then extruded.

It may be desired to incorporate the layered material with another material which is resistant to the temperatures and other conditions employed in the catalytic processes described herein. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with layered material, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with layered materials include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with layered materials also include inorganic oxides, notably alumina.

In addition to the foregoing materials, the layered materials can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided layered materials and inorganic oxide matrix vary widely, with the layered material content ranging from about 1 to about 90 percent by weight and more usually, particularly when the composite is prepared in the form of beads, in the range of about 2 to about 80 weight of the composite.

EXAMPLES

Example 1

The vacancy-containing titanometallate molecular sieve was synthesized by the following procedures. The layered precursor, alkali metal titanometallate, was prepared by high temperature solid state reaction of $Cs_2CO_3$ and $TiO_2$ in the stoichiometry of 1:10.4 ($Cs_{0.36}\square_{0.18}Ti_{1.82}O_4$). $Cs_2CO_3$ was ground to a fine powder (<100 mesh) then dried and stored in a vacuum oven at 180° C. $TiO_2$ was used as received. The solids (100.00 g $Cs_2CO_3$ and 127.87 g $TiO_2$) were ground to a homogeneous mixture which was fired at 650° C. for 600 min. followed by an additional 600 min. at 650° C. after regrinding. The layered product was ground after firing.

An aqueous slurry of this material (30% solid) was ball-milled for 6 hours. Exchange of cesium cations from the material was effected by treating the solid with 1M ammonium nitrate until cesium content was less than 150 ppm. The solid was then swollen by refluxing in excess neat butylamine at 78° C. for 24 hours using a Dean-Stark trap in the condensation column to remove $H_2O$ from the system.

The butylamine swollen solid was further swollen by refluxing in excess n-dodecylamine at 150° C. At this temperature the butylamine which is exchanged is removed as vapor from the reaction mixture.

Once the swelling of the materials was completed, pillars were formed by multiple tetraethylorthosilicate (TEOS)/$H_2O$ treatments. The dodecylamine swollen material was treated twice with TEOS prior to the initial $H_2O$ treatment. In the TEOS treatment, the solids were stirred in TEOS (5 g TEOS/g solid), while maintaining the reaction temperature at 80° C. under a slight flow of $N_2$ for 24 hours. The solids were then filtered and air dried. In the $H_2O$ treatment, the solids were slurried in $H_2O$ for 4 hours, filtered and air dried. The finished pillared product (porous molecular sieve) was obtained by calcination of the TEOS treated solids at 500° C. for 4 hours in flowing (3 v/v/min) air. This pillared material is a member of the MCM-27-□(Si) family, and is designated herein as VTM-A. Its chemical and physical properties are listed below.

| | |
|---|---|
| Ti, wt. % | 34.1 |
| $SiO_2$, wt. % | 43.6 |
| Surface area, $m^2/g$ | 901 |
| Adsorption, wt. % | |
| $H_2O$ | 42.0 |
| cyclo-$C_6$ | 1.6 |
| normal-$C_6$ | 27.7 |

Example 2

The VTM-A catalyst in Example 1 was evaluated for alkylation of isobutane with butene-2 conducted in a continuous stirred tank reactor. Prior to the testing, catalysts were crushed to a <100 mesh and pretreated at 400° C. for 3 hours in dry air. Then 10 grams of the catalyst was placed in a 300 cc stainless steel stirred autoclave and the reactor was filled with isobutane. The slurry was stirred at 1900 rpm and heated to 100° C. The pressure was kept at about 410 psig. After the desired temperature was reached, a feed with an isobutane/butene-2 ratio of 20/1 was continuously fed into the reactor at a butene weight hourly space velocity of 0.1. On-line samples were taken at various times on stream for the gas chromatographic analysis. The results are shown in the Table below.

Alkylation of isobutane with butene-2 at 100° C., 410 psig and 0.05 olefin WHSV with an isobutane/butene-2 ratio of 20:1

| | | |
|---|---|---|
| Time on stream, hours | 3.5 | 5.1 |
| Cutene Conversion, % | 100 | 100 |
| $C_5+$ Alkylate Yield (g $C_5+$/g olefin converted) | 1.59 | 1.62 |
| $C_5+$ Alkylate Distribution, wt. % | | |
| $C_5-C_7$ | 11.7 | 14.3 |
| $C_8$ | 82.9 | 79.8 |
| $C_9+$ | 5.4 | 5.9 |
| TMP/($C_8$-TMP)* | 7.0 | 6.2 |

Changes and modifications in the specifically described embodiments can be carried out without departing from the scope of the invention which is intended to be limited only by the scope of the appended claims.

What is claimed is:

1. A process for alkylating an olefin with an isoparaffin comprising contacting an olefin-containing feed in the presence of a thermally stable composition comprising layered metal oxide, wherein each layer of the metal oxide has the general formula $$[M_x\square_yZ_{2-(x+y)}O_4]^{q-}$$

wherein M is at least one metal of valence n wherein n is an interger between 0 and 7, □ represents a vacancy site, Z is titanium, and wherein $$q=4y-x(n-4),$$

and $$0<x+y<2$$

under process conditions of temperature from about 0° C. to about 500° C., pressure from about 0 to about 2000 psig, and olefin weight hourly space velocity (WHSV) sufficient to convert about 99 percent by weight of fresh olefin to alkylate product.

2. The process of claim 1 wherein said process conditions comprise temperature from about 25° C. to about 250° C., pressure from about 0 to about 2000 psig, and weight hourly space velocity (WHSV) from about 0.01 to about 10 $hr^{-1}$.

* * * * *